United States Patent [19]

Ogawa et al.

[11] Patent Number: 5,068,446
[45] Date of Patent: Nov. 26, 1991

[54] PROCESS FOR PREPARATION OF DIBROMOPROPYL ETHER COMPOUND HAVING HIGH MELTING POINT

[75] Inventors: Yoshikatsu Ogawa, Takatsuki; Haruhiko Hisada, Yao; Takeshi Kasahara, Sakai; Fumihiko Kizaki, Osaka; Masahide Yoshiya, Fujiidera, all of Japan

[73] Assignee: Marubishi Yuka Kogyo Kabushiki Kaisha, Osaka, Japan

[21] Appl. No.: 503,386

[22] Filed: Mar. 30, 1990

[30] Foreign Application Priority Data

Apr. 28, 1989 [JP] Japan .................. 1-107807

[51] Int. Cl.$^5$ .................. C07C 315/06; C07C 41/40
[52] U.S. Cl. ........................ 568/33; 568/641
[58] Field of Search .................. 568/33, 641

[56] References Cited

U.S. PATENT DOCUMENTS 3,842,033 10/1974 Brady et al. .................. 568/641
4,006,118 2/1977 Ogawa et al. .................. 568/33
4,777,297 10/1988 Ogawa et al. .................. 568/33

FOREIGN PATENT DOCUMENTS 57-289 1/1982 Japan .
55148144 10/1987 Japan .

OTHER PUBLICATIONS

Kirk–Othmer, Encyclopedia of Chemical Technology, Second Edition, vol. 6, pp. 484–494 (1965).

Primary Examiner—Mary E. Ceperley
Attorney, Agent, or Firm—Michael N. Meller

[57] ABSTRACT

A process for the preparation of a dibromopropyl ether compound having a high melting point, which comprises mixing a bis-dibromopropyl ether of tetrabromobisphenol-sulfone or tetrabromobisphenolpropane represented by the following general formula:

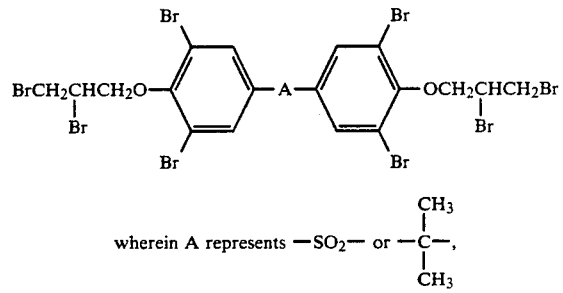

wherein A represents $-SO_2-$ or $-\underset{\underset{CH_3}{|}}{\overset{\overset{CH_3}{|}}{C}}-$, in the melted state with a crystallized product of said compound at a temperature lower than the melting point of the crystallized product, and holding the mixture at a temperature of 50° to 100° C.

According to this process, the dibromopropyl ether compound of a high melting point can be prepared without using an organic solvent.

5 Claims, 5 Drawing Sheets

DSC Chart No.1

DSC Chart No. 2

DSC Chart No. 3

DSC Chart No. 4

DSC Chart No. 5

PROCESS FOR PREPARATION OF DIBROMOPROPYL ETHER COMPOUND HAVING HIGH MELTING POINT

BACKGROUND OF THE INVENTION

1. Field of the Invention

The present invention relates to a process for the preparation of a dibromopropyl ether compound having a high melting point.

2. Description of the Related Art

It is known that a dibromopropyl ether compound represented by the following general formula:

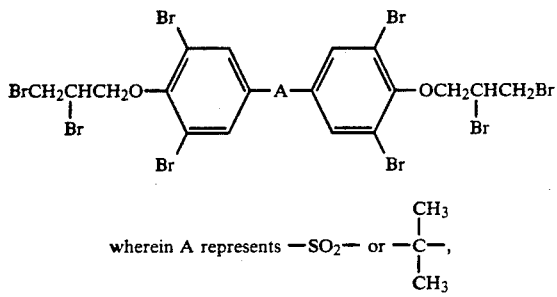

wherein A represents $-SO_2-$ or $-\underset{\underset{CH_3}{|}}{\overset{\overset{CH_3}{|}}{C}}-$, is a flame retardant. For example, Japanese Examined Patent Publication No. 50-35103 and Japanese Examined Patent Publication No. 62-49900 teach that a bis-dibromopropyl ether of tetrabromobisphenol-sulfone (TBS) and a bis-dibromopropyl ether of tetrabromobisphenol-propane (TBA) are valuable as a flame retardant for plastics. Furthermore, Japanese Examined Patent Publication No. 63-39585 and Japanese Examined Patent Publication No. 57-289 disclose processes for the preparation of these compounds.

More specifically, Example 5 of Japanese Examined Patent Publication No. 63-39585 discloses a process in which bis-(4-allyloxy-3,5-dibromophenyl)sulfone is dissolved in methylene chloride and reacted with bromine, methylene chloride is evaporated and a treatment is carried out at 105° C. under a reduced pressure (3 mmHg) to obtain a vitreous bis-dibromopropyl ether of TBS having a softening point of 50° to 53° C. Furthermore, in Japanese Examined Patent Publication No. 57-289, it is taught that a bis-dibromopropyl ether of TBA. is obtained by brominating 2,2-bis-(4-allyloxy-3,5-dibromophenyl)propane and this compound is a resinous product melting at 40° to 50° C. The reason why the melting point or softening points of the bis-dibromopropyl ether compounds of TBS and TBA are low and are about 40° to about 50° C. is that these compounds are not crystallized. It is taught in the foregoing patent publications that, if these compounds are recrystallized from solvents or are crystallized by adding poor solvents to solutions of these compounds in good solvents, products having a high melting point can be obtained.

When these compounds are used as flame retardants for plastics, in general, these compounds are powdered and mixed into pellets and the compositions are processed, but since the softening points are low, the following disadvantages arise:

(1) Where the compound is pulverized, the pulverization must be carried out at a low temperature not exceeding 15° C.

(2) Since the powder is readily blocked during transportation or storage, refrigerated transportation or storage in a refrigerated warehouse is necessary.

(3) When the compound is mixed with pellets of plastics, since the compound is fused in a Henschel mixer, an unsatisfactory mix is often obtained.

(4) When flame-retardant pellets are formed by using an extruding molding machine, bridging occurs in a hopper and a plastic material is not smoothly supplied.

(5) Since the softening points of plastics are greatly different from those of the compounds, the compounds are melted prior to the plastics in an extrusion molding machine, and therefore, the compounds slip and the biting becomes poor, with the result that a satisfactory mix is not obtained.

(6) When flame-retardant pellets are prepared by mixing the compounds into plastics, it is necessary to use plastics in the powder form and to use a twin-screw extruder.

Because organic solvents are used therein, the processes disclosed in Japanese Examined Patent Publication No. 63-39585 and Japanese Examined Patent Publication No. 57-289, that is, the process in which recrystallization from ethylene glycol monomethyl ether is carried out for obtaining a product having a high melting point, and the process in which methanol is added in a methylene chloride solution of the dibromopropyl ether compound to effect crystallization, are defective in the following points:

(1) Filtration and drying steps are necessary, and there is a risk of fire and problems of safety and hygiene. Moreover, it is necessary to use an apparatus for recovering the solvents.

(2) In the case of the bis-dibromopropyl ether of TBS, methylcellosolve and ethylcellosolve are excellent as the recrystallization solvent, but the recrystallized product must be recovered by filtration and dried. Since the boiling points of these solvents are high, at 124° C. and 134° C., respectively, heating is necessary for the drying, and as the solvent is contained in the crystallized product, a remelting of the crystallized product is caused by this heating. Therefore, after the filtration, it is necessary to replace the recrystallization solvent by an inert solvent such as methanol, and to dry the recrystallized product.

SUMMARY OF THE INVENTION

The inventors carried out research into the defects of the conventional processes, and as a result, succeeded in providing a process for preparing a dibromopropyl ether compound having a high melting point, without using an organic solvent.

More specifically, in accordance with the present invention, there is provided a process for the preparation of a dibromopropyl ether compound having a high melting point, which comprises mixing a bis-dibromopropyl ether of tetrabromobisphenol-sulfone or tetrabromobisphenol-propane represented by the following general formula:

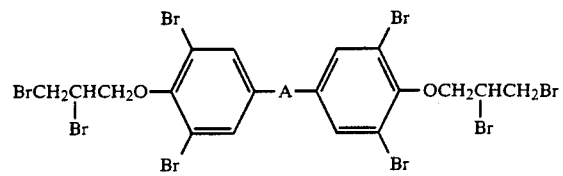

-continued

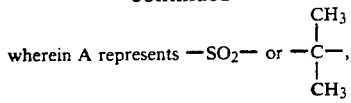

in the melted state with a crystallized product of said compound at a temperature lower than the melting point of the crystallized product, and holding the mixture at a temperature of 50° to 100° C.

DESCRIPTION OF THE PREFERRED EMBODIMENTS

Figure 1:
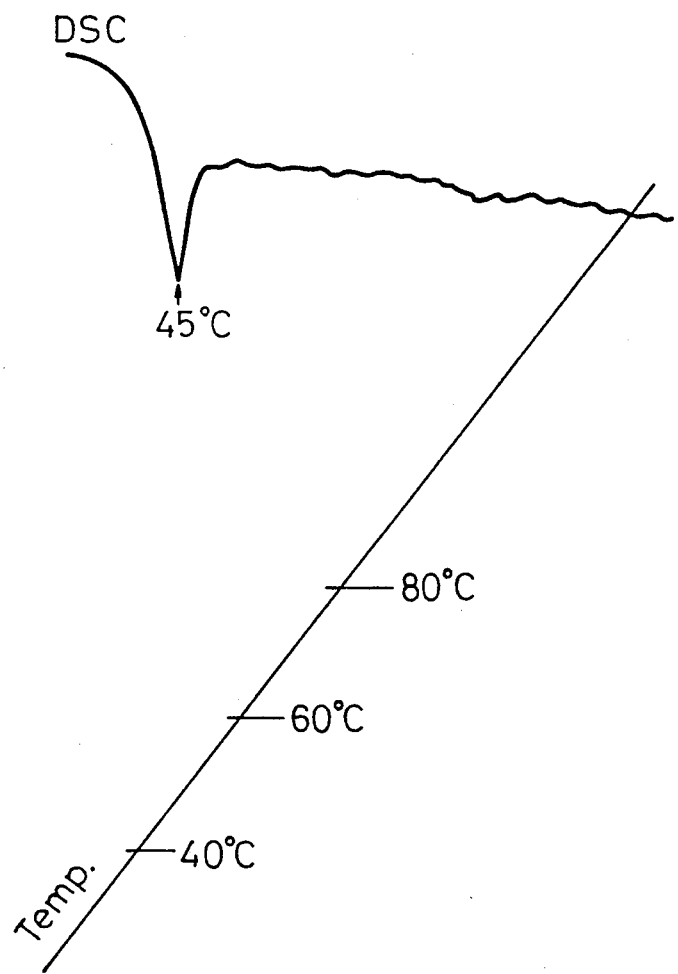
FIGS. 1 and 4 are DSC charts of low-melting-point samples.

A conventional preparation apparatus can be used when carrying out the process of the present invention.

Further, when carrying out the process of the present invention, a bis-allyl ether of TBS or a bis-allyl ether of TBA is dissolved in a solvent, for example, methylene chloride, and bromine is added to the allyl group and the addition reaction product is neutralized and washed with water. Then methylene chloride is removed by distillation and volatile components are removed by a reduced-pressure treatment at 100° to 120° C., a crystallized product of the dibromopropyl ether compound is added to the residue, and these are mixed at a temperature lower than the melting point of the crystallized product, preferably at a temperature of 80° to 100° C. The mixture is recovered from the vessel by customary procedures, and held at a temperature of 50° to 100° C., preferably 70° to 90° C., for at least 1 hour, preferably 3 to 15 hours. Alternatively, a method can be adopted in which the dibromopropyl ether compound having a low softening point is heated and melted, a crystallized product of the ether compound is added to the melt, and these are mixed, but the present invention is not limited to these operation methods.

The crystallized product of the bis-dibromopropyl ether of TBS or TBA used in the present invention is preferably a crystalline powder obtained by recrystallization or the like, although a powder or coarse powder obtained by pulverizing the high-melting-point product obtained according to the process of the present invention also can be used.

The amount of the crystallized product added is not particularly critical, but preferably the crystallized product is added in an amount of at least 0.01% by weight, more preferably at least 0.1% by weight, based on the dibromopropyl ether compound. If the amount of the crystallized product added is less than 0.01% by weight based on the dibromopropyl ether compound, a long time is needed to form a high-melting-point product.

The mixing of the crystallized product must be carried out at a temperature lower than the melting point of the crystallized product (the melting point of the crystallized product of the bis-dibromopropyl ether of TBS is 125° C. and the melting point of the crystallized product of the bis-dibromopropyl ether of TBA is 112° C.). If the mixing is carried out at a temperature higher than the melting point of the crystallized product, the crystallized product is melted and the intended high-melting-point product cannot be obtained. In general, the mixing is preferably carried out at a temperature of 80° to 100° C. If the mixing temperature is lower than 80° C., the viscosity of the dibromopropyl ether compound in the melted state increases and the mixing becomes difficult.

After the mixing of the crystallized product, the mixture is held at a temperature of 50° to 100° C., preferably 70° to 90° C., for at least 1 hour, preferably 3 to 30 hours. If the mixing temperature is lower than 50° C. or higher than 100° C., the intended product cannot be obtained. It is not necessary to maintain the temperature at a constant level, and the temperature may be changed in the range of 50° to 100° C. If the holding time is shorter than 1 hour, often the entire mixture is not converted to a uniform high-melting-point product. The mixture can be held at the above-mentioned temperature for more than 30 hours, but a substantial elevation of the melting point of the high-melting-point product is not attained and the process becomes disadvantageous from the economical viewpoint.

In the present invention, as the crystallized product of the dibromopropyl ether, there can be used a crystallized product of a bis-dibromopropyl ether of TBS and/or a bis-dibromopropyl ether of TBA, but where a crystallized product of the bis-dibromopropyl ether of TBA is used for the bis-dibromopropyl ether of TBS having a lower softening point, a long time is needed to elevate the melting point, and thus this procedure is not practically preferable. In the reverse case, a high-melting-point product can be obtained without particular trouble, but from the viewpoint of the purity of the product, preferably the crystallized product of the same compound as the intended product is used.

The present invention will now be described in detail with reference to the following examples, that by no means limit the scope of the invention.

EXAMPLE 1

Bis-(3,5-dibromo-4-dibromopropyloxyphenyl)sulfone (bis-dibromopropyl ether of TBS) (100 g) having a softening point of 50° to 53° C. was melted by heating at 95° C., a crystalline powder of bis-(3,5-dibromo-4-dibromopropyloxyphenyl)sulfone (melting point = 125° C.) recrystallized from methylcellosolve was added to the melt, and these ingredients were mixed. The mixture was held at various temperatures in a thermostat drier, and the melting points of the obtained products were measured. The results are shown in Table 1.

Figure 2:
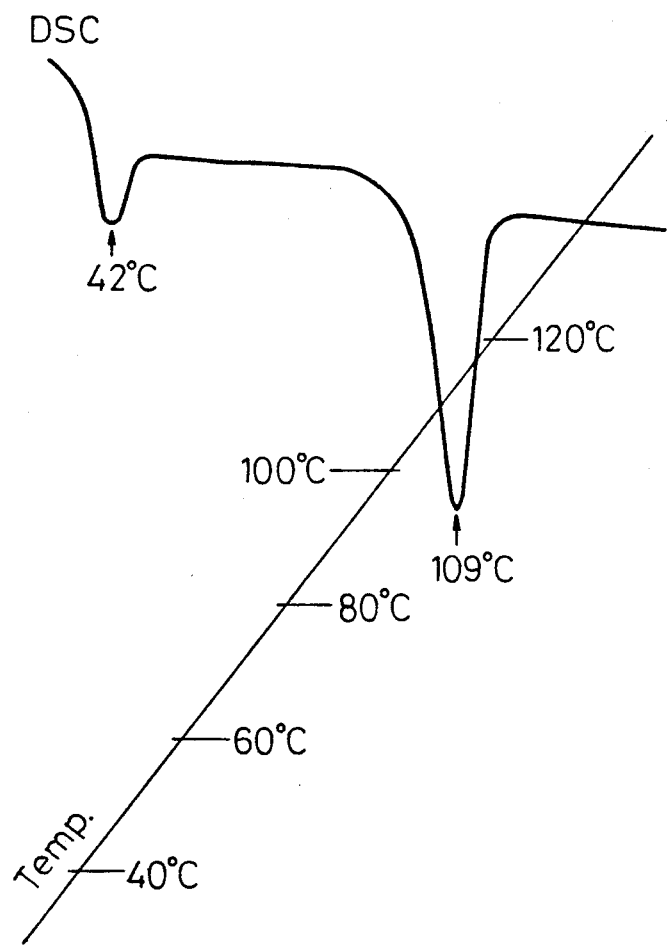
FIGS. 2, 3 and 5 are DSC charts of high-melting-point products obtained in the examples.

As seen from DSC chart No. 1 (FIG. 1), at the DSC measurement, the sample having a softening point of 50° to 53° C. shows one endothermic peak at about 45° C., but as seen from DSC chart No. 2 (FIG. 2), the high-melting-point sample having a melting point of 104° to 106° C., obtained in run No. 6, has a large endothermic peak at about 109° C. in addition to the peak appearing at about 42° C.

TABLE 1

| Run No. | Amount (%) of Crystalline Powder | Holding Temperature (°C.) | Holding Time (hours) | Melting Point (°C.) of Product | Remarks |
| --- | --- | --- | --- | --- | --- |
| 1 | 0.1 | 50 | 15 | 55–63 | present |

TABLE 1-continued

| Run No. | Amount (%) of Crystalline Powder | Holding Temperature (°C.) | Holding Time (hours) | Melting Point (°C.) of Product | Remarks |
| --- | --- | --- | --- | --- | --- |
| 2 | 0.1 | 60 | 15 | 57–65 | present invention |
| 3 | 0.3 | 70 | 3 | 75–106 | present invention |
| 4 | 0.1 | 70 | 7 | 102–106 | present invention |
| 5 | 0.1 | 70 | 15 | 103–106 | present invention |
| 6* | 0.1 | 80 | 15 | 104–106 | present invention |
| 7 | 0.1 | 90 | 15 | 75–105 | present invention |
| 8 | 0.1 | 100 | 10 | 60–62 | present invention |
| 9 | 0.05 | 70 | 15 | 102–106 | present invention |
| 10 | 1.0 | 80 | 7 | 103–107 | present invention |
| 11 | 0 | 50 | 15 | 50–53 | comparison |
| 12 | 0 | 70 | 15 | 50–53 | comparison |
| 13 | 0 | 90 | 15 | 50–53 | comparison |
| 14 | 0 | 100 | 15 | 50–53 | comparison |
| 15 | 0.3 | 40 | 15 | 50–53 | comparison |
| 16 | 0.3 | 110 | 15 | 50–53 | comparison |

*Sample subjected to DSC measurement.

EXAMPLE 2

Figure 3:
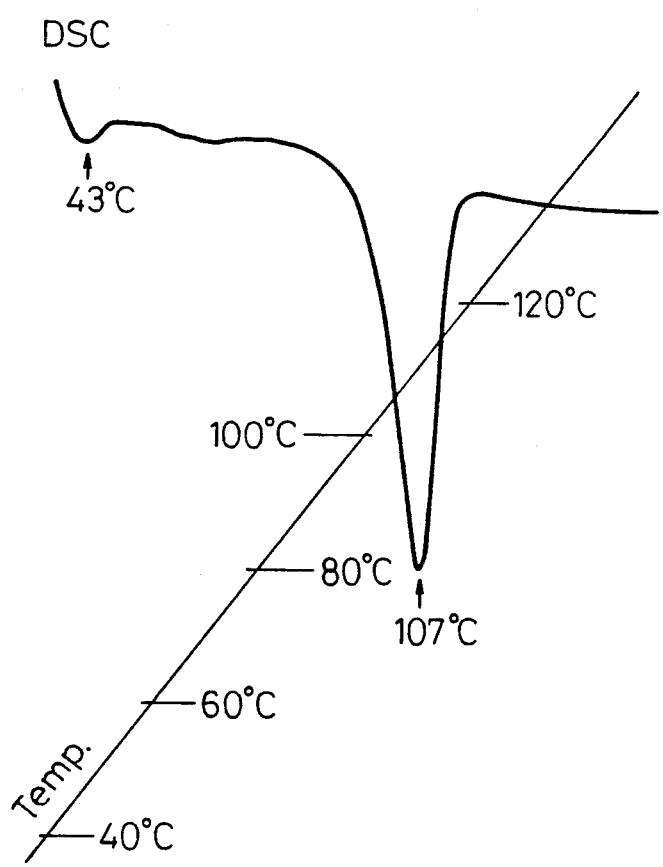

In 950 g of methylene chloride was dissolved 323 g (0.5 mole) of bis-(4-allyloxy-3,5-dibromophenyl)sulfone, and 162 g (1.01 moles) of bromine was added to the solution at 30° to 40° C. to effect reaction. Then the reaction mixture was washed with water, washed with a 0.5% aqueous solution of sodium bicarbonate and then washed with water, methylene chloride was removed by distillation, and the residue was treated at an inner temperature of 105° C. under a reduced pressure (3 mmHg). Then the inner temperature was lowered to 90° C., and 3 g of the crystalline powder having a melting point of 125° C., which was used in Example 1, was added to and mixed with the reaction product, and the mixture was charged into a beaker and held in an oven at 70° C. for 8 hours. The entire mixture was solidified and a product having a melting point of 104° to 107° C. was obtained. As seen from DSC chart No. 3 (FIG. 3), at the DSC measurement, the product has a small endothermic peak at about 43° C. and a large endothermic peak at about 107° C.

COMPARATIVE EXAMPLE

The preparation was carried out in the same manner as described in Example 2 except that the crystalline powder was not added. The obtained product showed a melting point of 50° to 53° C., and a high-melting-point product could not be obtained.

EXAMPLE 3

The preparation was carried out in the same manner as described in Example 2 except that the final treatment was carried out at an inner temperature of 105° C. under a reduced pressure (3 mmHg). Then the inner temperature was lowered to 90° C., and 3 g of a powder of the high-melting-point product (melting point = 104° to 107° C.) of the bis-(3,5-dibromo-4-dibromopropyloxy-phenyl)sulfone obtained in Example 2 was added to the reaction product. The mixture was charged into a beaker and held in an oven at 70° C. for 8 hours. The entire mixture was solidified and a product having a melting point of 102° to 106° C. was obtained.

EXAMPLE 4

2,2-Bis-(3,5-dibromo-4-dibromopropyloxyphenyl)-propane (bis-dibromopropyl ether of TBA) (100 g) having a softening point of 38° to 44° C. was heated at 95° C. and melted. A crystalline powder of 2,2-bis-(3,5-dibromo-4-dibromopropyloxyphenyl)propane (melting point = 112° C.) recrystallized from methylcellosolve was mixed into the melt, and the mixture was held at various temperatures in a thermostat drier. The melting points of the obtained products were measured. The results are shown in Table 2.

Figure 4:
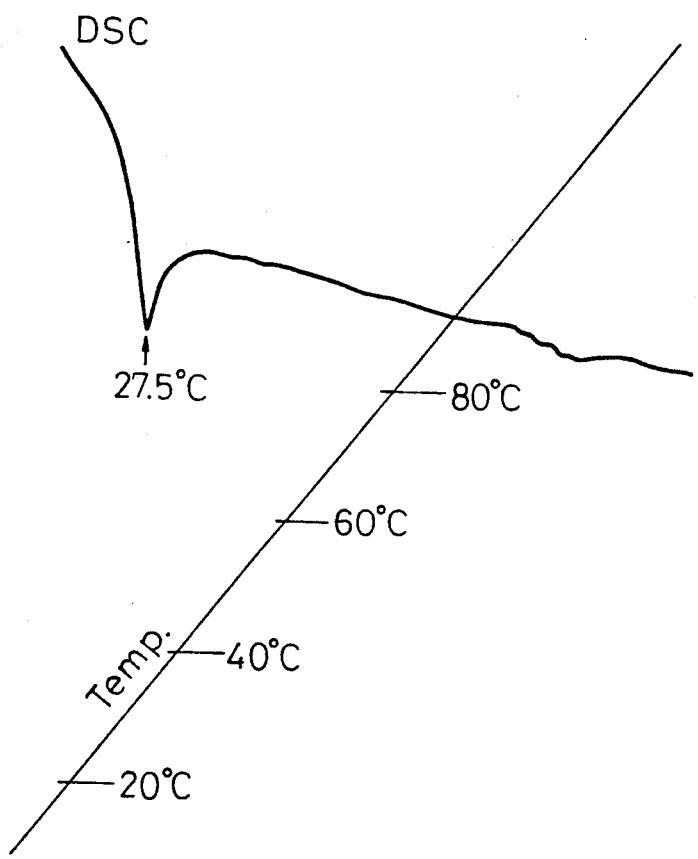
Figure 5:
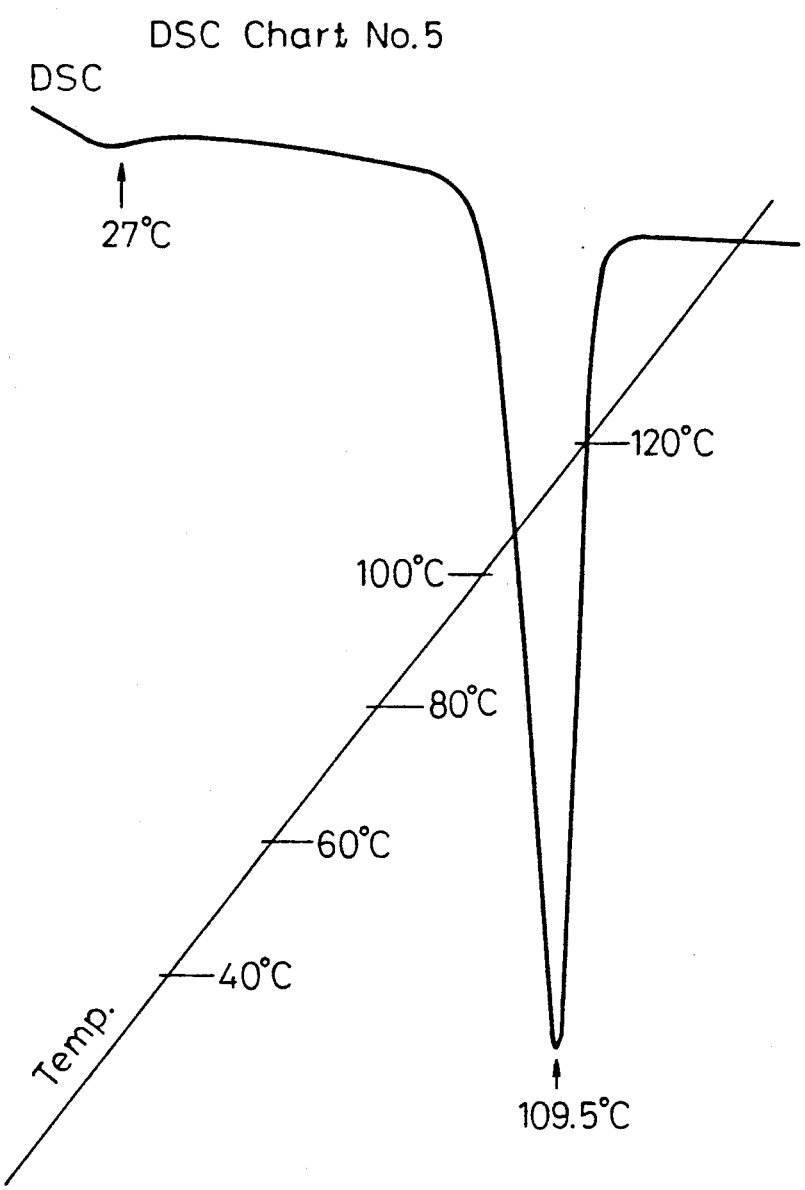

As seen from DSC chart No. 4 (FIG. 4), at the DSC measurement, the sample having a softening point of 38° to 44° C. shows only one endothermic peak at about 27.5° C., but the high-melting-point sample having a melting of 109° to 112° C., obtained in run No. 8, shows a large endothermic peak at about 109.5° C. while the endothermic peak at about 27° C. substantially disappears, as is seen from DSC chart No. 5 (FIG. 5).

TABLE 2

| Run No. | Amount (%) of Crystalline Powder | Holding Temperature (°C.) | Holding Time (hours) | Melting Point (°C.) of Product | Remarks |
| --- | --- | --- | --- | --- | --- |
| 1 | 0.1 | 50 | 15 | 51–61 | present invention |
| 2 | 0.1 | 60 | 10 | 65–72 | present invention |
| 3 | 0.3 | 70 | 3 | 83–109 | present |

TABLE 2-continued

| Run No. | Amount (%) of Crystalline Powder | Holding Temperature (°C.) | Holding Time (hours) | Melting Point (°C.) of Product | Remarks |
| --- | --- | --- | --- | --- | --- |
| 4 | 0.1 | 70 | 10 | 105–109 | present invention |
| 5 | 0.1 | 80 | 10 | 102–109 | present invention |
| 6 | 0.1 | 90 | 10 | 95–105 | present invention |
| 7 | 0.1 | 100 | 10 | 48–57 | present invention |
| 8* | 1.0 | 70 | 15 | 109–112 | present invention |
| 9 | 0.05 | 70 | 15 | 101–108 | present invention |
| 10 | 0 | 50 | 15 | 38–44 | comparison |
| 11 | 0 | 70 | 15 | 38–44 | comparison |
| 12 | 0.1 | 40 | 15 | 38–44 | comparison |
| 13 | 0.1 | 110 | 15 | 38–44 | comparison |

*Sample subjected to DSC measurement.

We claim:

1. A process for the preparation of a dibromopropyl ether compound having a high melting point, which comprises mixing a bis-dibromopropyl ether of tetrabromobisphenol-sulfone or tetrabromobisphenolpropane represented by the following general formula:

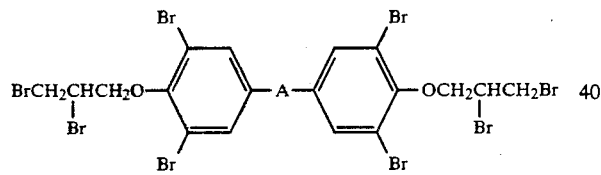

wherein A represents $-SO_2-$ or $-\underset{\underset{CH_3}{|}}{\overset{\overset{CH_3}{|}}{C}}-$, in the melted state with a crystallized product of said compound at a temperature lower than the melting point of the crystallized product, and holding the mixture at a temperature of 50° to 100° C.

2. A process according to claim 1, wherein said crystallized product is added in an amount of at least 0.01% by weight based on the weight of said dibromopropyl ether compound.

3. A process according to claim 1, wherein said dibromopropyl ether compound is mixed with said crystallized product at a temperature of 80° to 100° C.

4. A process according to claim 1, wherein said mixture is maintained at a temperature of 50° to 100° C. for at least 1 hour.

5. A process according to claim 4, wherein said mixture is maintained at a temperature of 70° to 90° C.

* * * * *